United States Patent [19]

Eckfeldt

[11] 3,998,591
[45] Dec. 21, 1976

[54] SPECTROCHEMICAL ANALYZER USING SURFACE-BOUND COLOR REAGENTS

[75] Inventor: Edgar Lawrence Eckfeldt, Ambler, Pa.

[73] Assignee: Leeds & Northrup Company, North Wales, Pa.

[22] Filed: Sept. 26, 1975

[21] Appl. No.: 617,265

[52] U.S. Cl. .......................... 23/253 R; 350/96 R; 350/96 WG; 356/209
[51] Int. Cl.² ................. G01N 21/48; G01N 31/22; G02B 5/12
[58] Field of Search ................... 23/253 R, 253 TP; 356/38, 51, 195, 209; 350/96 R, 96 WG

[56] References Cited
UNITED STATES PATENTS

| | | | |
|---|---|---|---|
| 3,431,411 | 3/1969 | Harrick | 356/51 X |
| 3,515,490 | 6/1970 | Dreyfus et al. | 356/244 |
| 3,582,209 | 6/1971 | La Rosa | 356/51 |
| 3,904,373 | 9/1975 | Harper | 23/253 TP |

OTHER PUBLICATIONS

Harrick, *Anal. Chem.,* vol. 36, pp. 188–191 (1964).
*Chem. and Engr. News,* Dec. 8, 1975, p. 13.

*Primary Examiner*—Robert M. Reese
*Attorney, Agent, or Firm*—William G. Miller, Jr.; Raymond F. MacKay

[57] ABSTRACT

A spectrochemical analyzer utilizing a transparent medium such as quartz which has a color reagent coating the surface. When light is directed into the transparent medium, the magnitude of internal surface reflection varies with the change in absorptivity resulting from a color change in the reagent in response to a change in the chemical condition of the sample. By measurement of the light transmitted by the transparent medium the chemical condition of the sample is measured.

11 Claims, 6 Drawing Figures

SPECTROCHEMICAL ANALYZER USING SURFACE-BOUND COLOR REAGENTS

BACKGROUND OF THE INVENTION

This invention relates to a spectrochemical analyzer of the type which utilizes colorimetric indicators responsive to specific chemical conditions. More specifically, this invention relates to spectrochemical analyzers which utilize optical means for determining the response of a color reagent to a change in a specific chemical condition.

The customary procedure for making a spectrochemical analysis using color reagents involves the use of a light transmission cell with the color reagent dissolved in the sample solution to be tested. By proper choice of the color reagents that method has been found to be highly specific and very sensitive and the apparatus involved is usually simple and relatively inexpensive. In the conventional approach to colorimetry, however, complicated sample preparations are frequently necessary. The conventional approach has the disadvantage of requiring that the color reagent be dissolved in the sample solution and therefore the color reagent be dissolved in the sample solution and therefore the color reagent is lost when the sample is discarded. Additionally, it is necessary that the concentration of the color reagent in the sample solution be controlled for consistent results. The conventional system also becomes difficult to apply in installations requiring long term, unattended, automatic operation and it is difficult to eliminate particulate interference, thus making it difficult to make measurements on sample solutions having any significant degree of opacity due to particulate matter. Also the conventional approach has problems with regards to calibration drift resulting from the gradual dirt deposition on cell windows.

SUMMARY OF THE INVENTION

In carrying out this invention there is provided a spectrochemical analyzer which comprises a light conductor which has a portion of its surface coated with a color reagent responsive to change its light absorption quality in accordance with the magnitude of a specific chemical condition of a sample in contact with that surface. The analyzer includes means for directing light through the conductor and means for detecting changes in the intensity of the light transmitted by the light conductor in response to changes in the light absorption quality at the coated surfaces due to changes in the chemical condition of the sample.

From the above broad description of the invention it will be evident that this invention uses a thin layer of color reagent on the surface of a light pipe so that when the light pipe is immersed in the sample the reagent will respond to the specific chemical condition of the sample to be determined and will change its light absorportion properties accordingly. An optical measurement is made by using internal reflection phenomena, for as the absorption properties of the thin layer on the surface of the light pipe change the amount of internally reflected light which is transmitted by the light pipe will change and the change can therefore be measured as being indicative of the change in chemical condition of the sample. Although this invention generally contemplates the use of light absorption in the visible region, it will be evident that the same approach can be utilized in the infrared and ultraviolet regions. Hence for the purposes of this application the term "light" covers the range of frequencies spanned by those three regions as well as the visible region. Likewise, this invention contemplates not only a physical coating containing the color reagent but also chemically bound color reagents. Thus the term "coating" is used herein to denote both physical and chemical bound coatings.

Since the color reagent is, as mentioned above, attached to a solid structure and not dissolved in the sample solution the reagent in this invention is not lost when the sample is removed and the concentration of the reagent remains at a predetermined fixed level which can be an effectively high concentration level. As a result, the analytical procedure and instrumentation utilizing this invention are of a simplified nature and make possible a reduction in the cost of operation as well as an improvement in accuracy and sensitivity along with a reduction in maintenance requirements when compared with the conventional approach to colorimetry.

Using the approach of the present invention the optical system and the sample system are more completely separated from each other than in conventional colorimetry and the measurements of light energy will therefore be more stable, more reproducible and more free from sample interference. These qualities, of course, make the equipment utilizing this invention more adaptable to long term, unattended, automatic operation. In addition the elimination of particle interference can be so effective that measurements can be made on sample materials that are completely opaque due to particulate matter and the calibration drift commonly encountered in the instrumentation arising from the deposition of dirt on cell windows is avoided.

The spectrochemical analyzer of the present invention can be used, for example, in pH measurements as an alternative to the electrometric, glass electrode, method. The present invention has considerable advantages over the electrometric approach. For example, there are no liquid junction errors, low maintenance can be expected since there is no potassium chloride solution to refill; similarly, there is no salt contaminating discharge into the sample. The method would provide apparatus of rugged construction which would have a long life and which would be steam sterilizable and would have the characteristics of being non-toxic and harmless as a sensor to humans and animals.

The apparatus of the present invention likewise has advantages in analyzing gas samples. By conventional colorimetry gas samples would normally be measured by first absorbing the gas sample in a liquid that contains the color reagent and then measuring the absorbance change. That type of measurement is more complicated than the measurement with liquid samples because of the need to retain quantification information throughout the gas-to-liquid transition. Utilizing the present invention, the need for a liquid is dispensed with and the optical sensor can provide a simple solid state device which responds specifically to a constituent partial pressure change in the gaseous sample.

The present invention makes use of the fact that light traveling inside a transparent high-index medium undergoes internal reflection at a surface with some of the light energy in the region where reflection takes place emerging from the high-index medium and entering the color reagent layer, so that the amount of internal reflection becomes quantitatively related to the absorption characteristic of the material on the surface of the transparent medium. The color reagent layer is made thick enough to provide an adequate quantitative effect on the light traveling inside the high-index medium to give good signal to noise ratio, and thin enough to provide rapid diffusion exchange between sample and color reagent to give fast color response to sample concentration changes. The thickness of the color reagent layer may range from monomolecular up to a micron or more, depending on the extinction coefficient of the color reagent and its effective concentration in the layer. Thicker layers rather than thinner ones may be preferred for secondary reasons, as will be described later in connection with filtering of particulates and screening of ambient light.

BRIEF DESCRIPTION OF THE DRAWINGS

FIGS. 1A and 1B taken together show one form of the invention in which the light beam follows a defined path through the transparent high-index medium.

Figure 1:
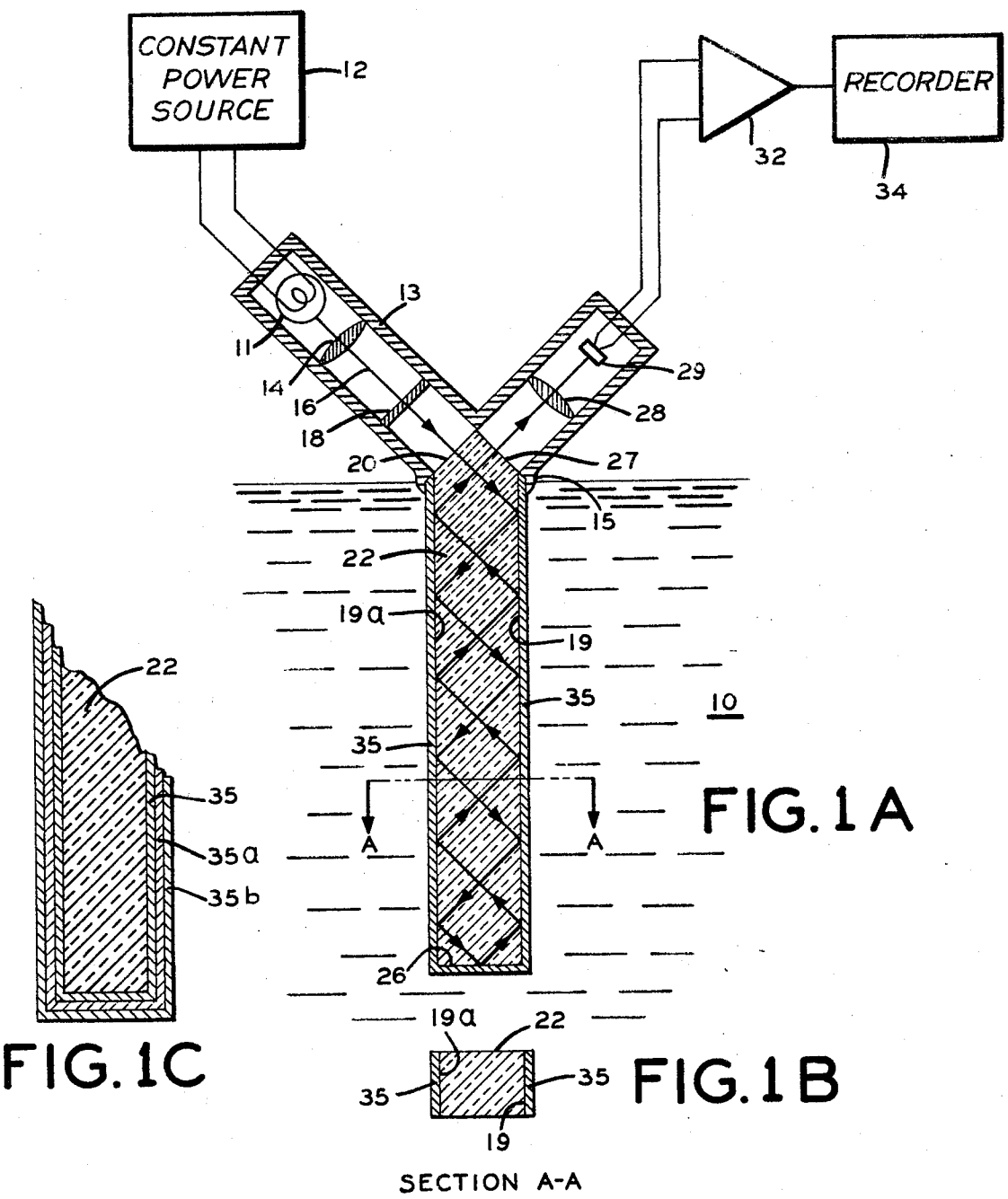
FIG. 1 is made up of FIGS. 1A, a section A—A from that figure shown as FIG. 1B, and a variation of FIG. 1A shown as FIG. 1C.

Color reagent molecules can be attached by covalent bonding to the surface of a light conducting material such as quartz, glass or organic polymeric material, using well known principles and techniques. In convalent bonding, a strong chemical linkage is established between the surface layer and substrate material, which results in permanent attachment of the surface layer. One such technique for covalently bonding acid-base color-change molecules to glass surfaces to make permanent reusable pH indicators has been described by G. Bruce Harper (Analytical Chemistry, 47, 348 (1975)). According to Harper's publication, reusable glass bound pH indicators may be made in whatever form is convenient for a particular laboratory operation, e.g., using as substrate glass wool, glass stirring rods, filter sticks, disks, or glass fragments. To obtain best results, the glass surface prior to attaching the indicator should be suitably conditioned, as by etching, or a sintered or porous glass can be used. In this technique, he uses silane coupling agents and gives procedural details to produce a variety of different indicator systems, having pH color change points ranging from about pH 1 to 11.

The work of Harper has been confirmed in the inventor's laboratory where a number of pH color change molecules have been attached by covalent bonding to glass surfaces. Quartz rods have been used in addition to glass substrates and these have the advantage over glass, for purposes of the present invention, of possessing excellent optical clarity. The intensity of color resulting from the bonded molecules on quartz has been augmented by first giving the surface of the quartz a special treatment. The rod is coated with a thin layer of a somewhat diluted colloidal silica solution containing one or two percent of ethylene glycol and dried thoroughly. The coated rod is then subjected to heat treatment in a furnace at 600°to 800° C. This treatment produces a thin layer of about a micron thickness of sintered colloidal silica particles on the surface of the rod.

It should be understood that a wide variety of techniques and procedures can be used to produce the desired layer of firmly attached color change molecules to the light pipe surface to carry out the present invention. For purposes of the present disclosure, the procedures described by Harper will serve to produce satisfactory results.

The layer 35 may optionally have additional functions. For example, the layer 35 may also serve to function as a mechanical screen or filter to exclude particulates from the region adjacent the light conducting medium where the light absorption takes place. If desired, a second layer 35a (FIG. 1C) of material such as a conventional polymeric plastic of several microns thickness may be placed on top of the primary layer of color reagent with the primary function of providing a barrier to particles. Such a second layer is selected to be porous to provide molecular diffusion therethrough of the species to be measured.

Protection of the optical probe formed by this apparatus from the interfering effects of ambient light can be accomplished by using a thin subsidiary layer of material opaque to light but permeable to the species being measured. That material can be an adherent layer of porous polymeric material containing finely divided opaque particles such as carbon black applied over the color reagent layer 35 or over the above mentioned second layer 35a as layer 35b, shown in FIG. 1C. It will be desirable, of course, to maintain the total thickness of the single or multiple layers applied to the medium 22 at a minimum thickness as the thickness of the layers will affect the speed at which the diffusion interchange can be accomplished and it is desirable to minimize the delay in diffusion interchange so as to promote equilibrium between the sample and the sensitive reagent on the medium 22 so that the speed of response of the system to changes in concentration of the medium can be high. Diffusion interchange will be very rapid if the thickness of the overall porous layer is kept less than 4 or 5 microns.

As pointed out, the transparent medium 22 with its thin layer of color reagent on the surface, namely the layer 35, comprises an optical probe which can be immersed as shown in FIG. 1 in a sample solution such as the liquid solution 10 when making a measurement such as a pH measurement of that solution. The diffusible constituents of the sample will rapidly penetrate into the thin layer 35 and the constituent to be measured will act upon the color reagent of that thin layer causing its absorptivity to change in degree dependent upon the constituent concentration as, for example, depending upon the pH of the sample 10. As a result the light beam 16, which may be of a favorable color as determined by the color filter 18, will be absorbed to a lesser or greater degree at each point in the medium 22 at which internal reflection occurs. The total amount of light reaching the detector 29 will thus depend ultimately upon the concentration of the constituent in the sample 10 as, for example, its pH. The electrical signal from the light detector 29 is amplified by amplifier 32 which is connected to provide its output to the recorder 34 so that the concentration of the constituent in the sample can be recorded. It is, of course, not necessary to use a recorder such as in FIG. 1, for in some applications a simple indicator will be adequate.

In FIG. 1B there is shown a section of the optical probe taken at A—A which shows that the medium 22 is rectangular in cross section having two opposite faces 19 and 19a covered with a thin layer of color reagent, namely the layers 35.

In the construction of the optical probe of FIG. 1A it is possible to so arrange the probe so that the medium 22 and its associated color reagent coating 35 can be removed from the optical assembly so that another medium with a different type of coating can be substituted when it is desirable that the probe be adaptable for the measurement of a different constituent. With such an arrangement the interchange of the immersible portion of the probe, namely the medium 22, makes possible the use of different color reagents for the measurement of different constituents while utilizing a single optical system for those measurements.

Figure 2:
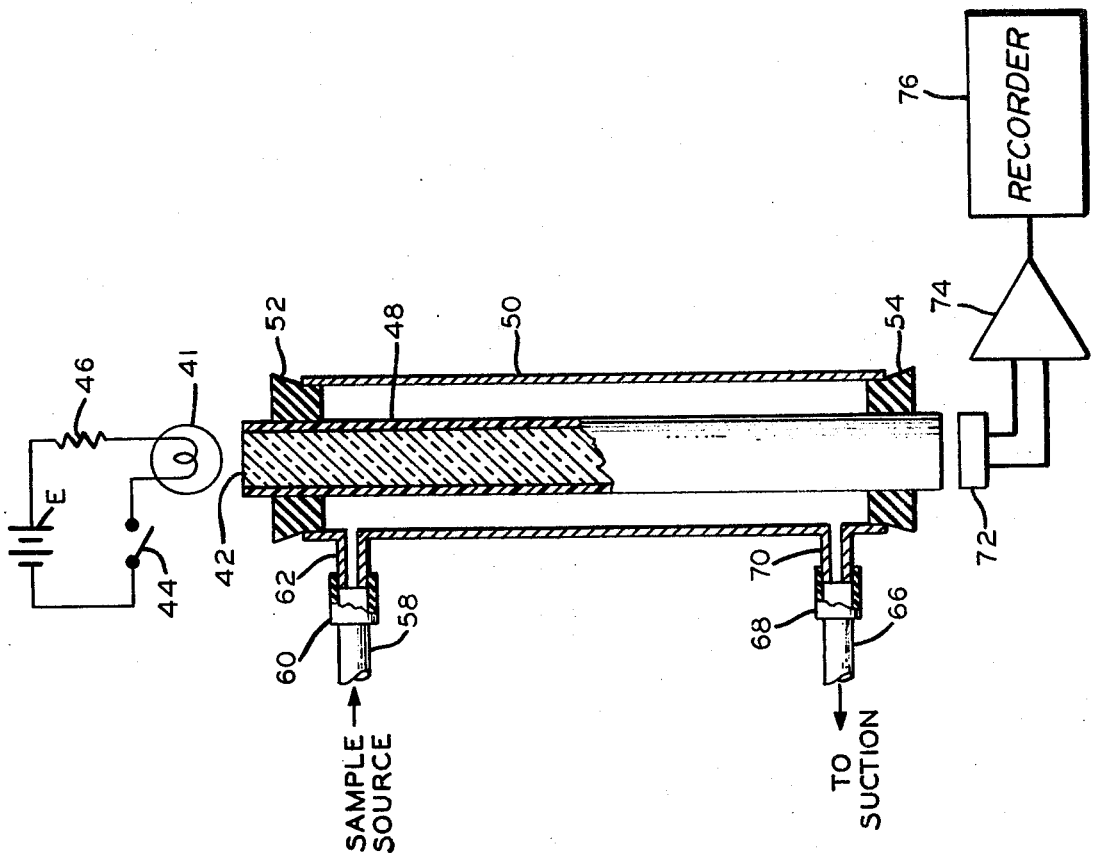
FIG. 2 shows another form of the invention in which the light follows a somewhat random path through the transparent high-index medium.

The form of the invention shown in FIG. 2 will be described as applied to gaseous samples, however, it will be evident that the same apparatus can also be used with liquid samples. In FIG. 2 a light source such as bulb 41 can be utilized to provide the light directed into the medium 42. The medium 42 is preferably a transparent medium of high refractive index such as quartz, glass or clear plastic material as mentioned with regard to FIG. 1. As shown in FIG. 2, the bulb 41 is energized from a potential source E upon closure of the switch 44 which completes the circuit to allow current to flow from the source E through the bulb and through the optional resistor 46 which may be selected to have the necessary value to provide the desired current through bulb 41.

The medium 42 is covered by a thin layer 48 of material containing or consisting of the color reagent. The medium 42 may preferably be cylindrical in shape and completely covered with the color reagent 48 and placed as shown in FIG. 2 in a surrounding cylindrical container 50 where it is retained in a centrally located position by the use of the stoppers 52 and 54. The space between the container 50 and the medium 42 then provides the space for the gaseous sample whose chemical constituents are to be determined to circulate in contact with the color reagent contained in the thin layer 48 around the medium 42. The gaseous sample is introduced from a sample source through the tube 58 which is connected as by a rubber connector 60 to the inlet port 62 of the cylindrical envelope 50. The sample is drawn into the envelope 50 by suction applied to the tube 66 which is shown connected by the rubber connector 68 to the outlet port 70 of the envelope 50. Thus, by virtue of the suction applied to the tube 66 the gaseous sample is drawn through the tube 58 into the envelope 50 and is circulated around the medium 42 in contact with the thin layer 48 which contains the color reagent selected to be responsive to the chemical constituent of the sample to be determined.

The light directed into the medium 42 will undergo internal reflections at the surface of the medium and the absorptive qualities of the coating 48 will determine the amount of light which will be transmitted through the medium 42 to the light detector 72. The amount of light transmitted is sensed by the detector 72 which is connected by way of amplifier 74 to provide a signal to recorder 76 indicative of the intensity of the light received by the detector 72. Thus the recorder 76 will provide a record of the concentration of the constituents detected by the color reagent in the coating 48.

The particular construction shown in FIG. 2 has been utilized to detect the concentration of ammonia in an ammonia gas analyzer by having the light conducting rod 42 coated with an acid-base indicator 48. The apparatus constructed in accordance with FIG. 2 utilized a plexiglass rod of 3/16 of an inch diameter and 5 inches in length coated with a coating 48 prepared as described below.

In preparing the coating 48 a stock solution of a dye-collodion mixture was prepared by taking 9.0 grams of the stock collodion and adding a 0.37 grams of the powder bromthymol blue dye and 20 ml. of ether with 20 ml. of grain alcohol.

The stock collodion was itself made by using 22 grams of Parlodion (a purified pyroxalin such as Merck's No. 6552) strips which were placed in a beaker along with 50 ml. of ether (ethyl) and 50 ml. of grain alcohol (190 proof). After allowing the above solution to stand overnight, 15 more ml. of each solvent was added and the mass was stirred several times.

Two dilutions of the stock solution were made. The first was composed of 24 ml. of stock solution plus 10 ml. of ether and 10 of alcohol. The second was composed of 24 ml. of the first solution plus 10 ml. of ether and 10 ml. of alcohol. These solutions were designated as concentrated, dilute and very dilute. It was found that a coated plexiglass rod and a coated quartz rod using the above mentioned solutions showed a definite quantitative relationship between the light intensity recorded by recorder 76 and the concentration of ammonia vapor drawn into the envelope 50.

While the above example sets forth one method by which the desired color reagent can be attached to the light transmitting medium in the apparatus of the present invention, it will be evident that the color reagent can be attached in other ways which can be considered more permanent and less subject to deterioration such as by covalent bonding.

Color reagents are presently available for conventional colorimetry measurements of ammonia in gas samples, as mentioned above, as well as for pH measurements of liquid samples and many other types of chemical measurements. Those reagents can be adapted for use in the apparatus of the present invention by suitably binding the desired color reagent to the surface of the light transmitting medium.

Figure 3:
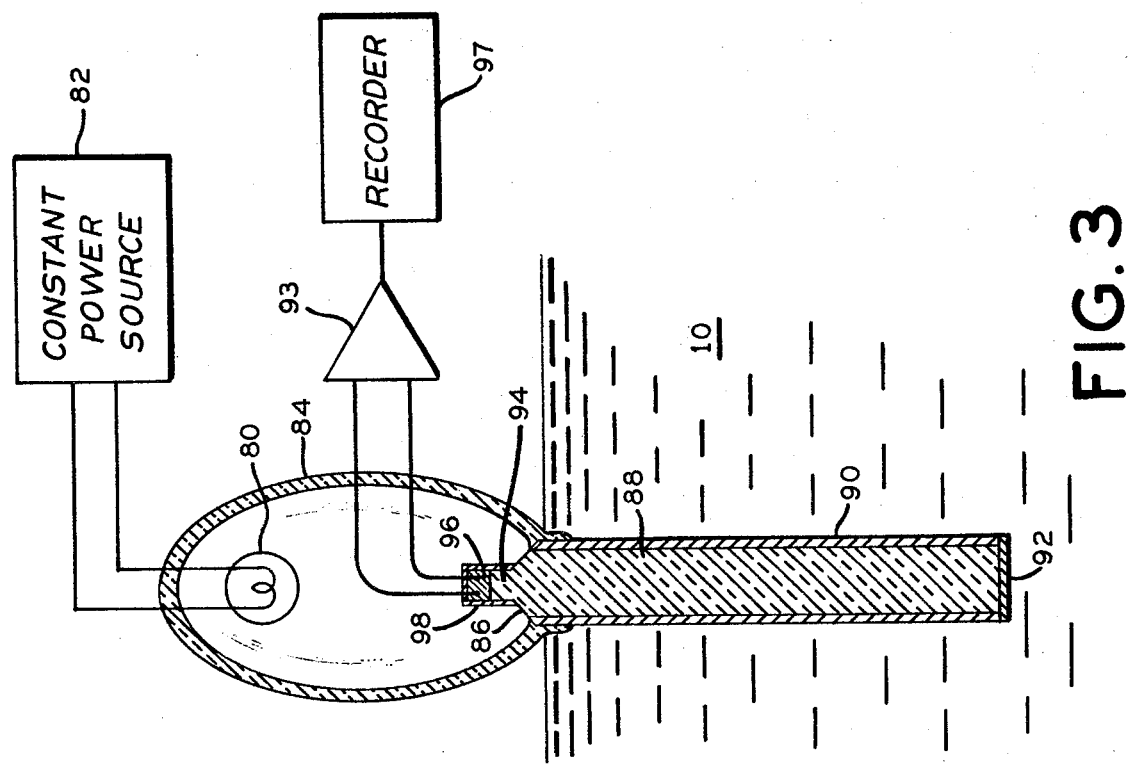
FIG. 3 still another form of the invention in which the light follows a random path. Description of the Preferred Embodiments Although the arrangement of FIG. 1 is also applicable to gaseous samples, it is shown as it might be applied to the analysis of a liquid sample 10. The analysis may, for example, be an analysis of the pH of the liquid sample 10. For that analysis the analyzer is shown utilizing a collimated beam of light that passes through the optics in the housing 13 of the analyzer in a defined path from source 11 which is shown as a light bulb connected to obtain power from a constant power source 12. The light from the source 11 is collimated by the lens 14 to form a beam 16 which passes through the color filter 18. The beam than passes through the face 20 of the transparent medium 22 joined to the housing 13 at the shoulder 15. That transparent medium may, for example, be made of any material having a high refractive index such as quartz, glass or clear plastic. As shown, the beam 16 is reflected internally on opposite faces 19 and 19a of the medium 22. The angle of incidence of the beam 16 to the surface is peferably 45°, so that the beam undergoes a number of such reflections until it strikes the bottom face 26 which reflects the beam in an upward direction so that it undergoes a similar series of internal reflections until the beam emerges from the face 27 of the transparent medium and passses through focusing lens 28 which focuses the light beam on the light detector element 29. The side and bottom faces of the transparent medium 22 are provided with a thin layer 35 containing a color reagent as required for providing a color change and a corresponding change in light absorption in response to changes in a chemical condition, such as the pH, of the sample 10.

FIG. 3 shows a form of the invention which, like the embodiment of FIG. 1, is particularly applicable to liquid analysis, such as for the pH of sample 10. The light source 80, shown as a simple bulb drawing its power from a constant power source 82, is positioned in an ellipsoidally shaped reflective housing 84. The light from source 80 is reflected downward and passes through the annular end surface 86 of the cylindrically shaped transparent medium 88, which as in FIG. 1 can be quartz, glass or clear plastic. Light enters the medium 88 from random directions, however, a portion of the light reflects from the surface of medium 88 where it is covered with the color reagent layer 90. Some of that reflected light reaches the bottom of the cylinder where it is reflected upward by the mirror 92 located at the bottom end of medium 88. Some of the light reflected by mirror 92 enters the neck region 94 and passes through the surface at the upper end of the neck where it strikes the light detector 96. The opaque cap 98 prevents light from inside the housing 84 from striking the detector 96.

It will be evident that the apparatus of FIG. 3, like that of FIG. 1, depends upon the change in color of the color reagent layer 90 to change the absorption properties of layer 90 and thus vary the light intensity reflected back to detector 96 in relation to the magnitude in the liquid sample 10 of the chemical characteristic to which the color reagent responds.

The output of detector 96 is supplied to amplifier 93 which in turn provides an input to recorder 97 which records the magnitude of the chemical quantity detected by detector 96.

As is the case with previous embodiments, the color reagent layer 90 may be covered with additional layers such as a layer to provide a barrier to particles in sample 10 and/or a layer for providing the necessary opacity to keep ambient light from interfering with the measurement of the output of detector 96.

What is claimed is:

1. A spectrochemical analyzer comprising;
   a light conductor with a portion of its surface coated with a color reagent responsive to change the light absorption quality of said reagent in accordance with the magnitude of a specific chemical condition of a sample in contact with said surface,
   means for directing light through said conductor so that multiple internal reflections occur at the coated portion of the surface, and
   means for detecting changes in the intensity of the light transmitted by said light conductor in response to changes in the light absorption quality at said coated surface due to changes in said chemical condition.

2. Apparatus as set forth in claim 1 in which the light conductor is a cylindrical rod having a reflective coating on one end and the means for directing light is positioned to direct the light from the other end through the conductor along random paths so that said light is reflected back to said other end and said means for detecting changes in the intensity of the light transmitted is positioned at said other end for responding to changes in the light absorption quality of the coated surface.

3. Apparatus as set forth in claim 1 in which said light conductor is coated with a porous coating over said color reagent coating so as to form a barrier to particles in the sample while allowing molecular diffusion of the sample therethrough.

4. Apparatus as set forth in claim 1 in which said light conductor is coated with a porous opaque coating over said color reagent to shield said conductor from ambient light.

5. Apparatus as set forth in claim 1 in which said chemical condition is pH.

6. An analyzer as set forth in claim 1 in which the light conductor is a cylindrical rod with the means for directing the light being positioned to direct the light into one end and the means for detecting changes of intensity of the light transmitted being positioned to receive the transmitted light at the other end of the rod.

7. An analyzer as set forth in claim 6 in which the light conductor is surrounded by an envelope having an inlet and outlet port adapted to receive a gas for flow through the space between said rod and said envelope.

8. An optical indicator of the chemical condition of a sample fluid comprising;
   a light conductor for insertion into said fluid whose condition is to be measured, said light conductor having attached to its outer surface for contact with said fluid a colorimetric reagent sensitive to changes of the chemical condition of said fluid,
   means for directing a source of light for transmission through said light conductor so that multiple internal reflections occur at the interface of said light conductor and said reagent, and
   means for detecting changes in the intensity of the light transmitted through said light conductor in response to changes in the color of said colorimetric reagent with changes in the chemical condition of said fluid.

9. Apparatus as set forth in claim 8 in which said chemical condition is pH.

10. Apparatus as set forth in claim 8 in which the light conductor has a rectangular cross section with opposing sides and one end having the color reagent attached thereto.

11. Apparatus as set forth in claim 10 in which said means for directing the light source for transmission through said light conductor includes
    means for providing a collimated light beam directed into one end of said light conductor so as to strike an internal surface to which the color reagent is attached at an angle which will produce multiple internal reflections between said opposing surfaces as the light beam goes to the end of the transparent medium and returns.

* * * * *